(12) United States Patent
Uram et al.

(10) Patent No.: US 11,337,598 B2
(45) Date of Patent: May 24, 2022

(54) LASER VIDEO ENDOSCOPE

(71) Applicant: Beaver-Visitec International, Inc., Waltham, MA (US)

(72) Inventors: Martin Uram, Middletown, NJ (US); Paula Ender, Middletown, NJ (US)

(73) Assignee: Beaver-Visitec International, Inc., Waltham, MA (US)

(*) Notice: Subject to any disclaimer, the term of this patent is extended or adjusted under 35 U.S.C. 154(b) by 133 days.

(21) Appl. No.: 16/365,853

(22) Filed: Mar. 27, 2019

(65) Prior Publication Data
US 2019/0216306 A1 Jul. 18, 2019

Related U.S. Application Data

(63) Continuation of application No. 14/966,151, filed on Dec. 11, 2015, now abandoned, which is a
(Continued)

(51) Int. Cl.
*A61B 1/07* (2006.01)
*A61B 1/04* (2006.01)
(Continued)

(52) U.S. Cl.
CPC ............ *A61B 1/07* (2013.01); *A61B 1/00167* (2013.01); *A61B 1/042* (2013.01); *A61B 3/156* (2013.01); *A61F 9/008* (2013.01)

(58) Field of Classification Search
CPC ............ A61B 1/00195; A61B 1/00117; A61B 1/0126; A61B 1/00013; A61B 1/00043;
(Continued)

(56) References Cited

U.S. PATENT DOCUMENTS 3,858,577 A 1/1975 Bass et al.
3,941,121 A 3/1976 Olinger et al.
(Continued)

FOREIGN PATENT DOCUMENTS

DE 19542955 A1 5/1997
EP 0512592 A1 11/1992
(Continued)

OTHER PUBLICATIONS

Gangi et al., Percutaneous Laser Photocoagulation of Spinal Osteoid Osteomas under CT Guidance, NJNR Am J Neuroradiol 19: 1955-1958, Nov. 1998.
(Continued)

*Primary Examiner* — Alexandra L Newton
*Assistant Examiner* — Alexandra Newton Surgan
(74) *Attorney, Agent, or Firm* — Budzyn IP Law, LLC

(57) ABSTRACT

Laser video endoscope has laser guide, illumination guide and image guide which extend through optical probe and through hand piece that supports the probe. Hand piece is connected by optical fiber cable to laser energy source and illumination source. Image is transmitted from hand piece to image processing interface by camera assembly optically coupled and mounted directly to hand piece and via electrical cable extending from camera assembly. Camera and its electrical cable can be uncoupled from hand piece and reused. The rest of the product, including probe and hand piece, can be disposed of after each medical routine. Probe can have proximal portion and distal portion such that proximal portion extends from distal end of hand piece, and outside diameter of proximal portion as measured at least near the distal end of hand piece is greater than the outside diameter of the distal portion.

8 Claims, 20 Drawing Sheets

Related U.S. Application Data continuation-in-part of application No. 13/084,789, filed on Apr. 12, 2011, now abandoned, and a continuation-in-part of application No. 13/314,371, filed on Dec. 8, 2011, now Pat. No. 10,226,167, which is a continuation-in-part of application No. 12/779,214, filed on May 13, 2010, now abandoned.

(51) Int. Cl.
  *A61B 1/00* (2006.01)
  *A61F 9/008* (2006.01)
  *A61B 3/15* (2006.01)

(58) Field of Classification Search
  CPC . A61B 1/00105; A61B 1/00165; A61B 1/042; A61B 2090/306; A61B 1/07; A61B 1/00126; A61B 1/0638; A61B 18/22; A61B 1/00167; A61F 9/008
  USPC ....... 600/108, 109, 112, 130, 132, 136, 160, 600/175, 178, 179, 181, 182
  See application file for complete search history.

(56) References Cited

U.S. PATENT DOCUMENTS

| | | | |
|---|---|---|---|
| 4,072,147 A | 2/1978 | Hett | |
| 4,170,997 A | 10/1979 | Pinnow et al. | |
| 4,448,188 A | 5/1984 | Loeb | |
| 4,537,193 A | 8/1985 | Tanner | |
| 4,589,404 A | 5/1986 | Barath et al. | |
| 4,604,992 A | 8/1986 | Sato | |
| 4,607,622 A * | 8/1986 | Fritch | A61B 1/042 600/108 |
| 4,624,243 A | 11/1986 | Lowery et al. | |
| 4,671,273 A | 6/1987 | Lindsey | |
| 4,697,210 A | 9/1987 | Toyota et al. | |
| 4,700,694 A | 10/1987 | Shishido | |
| 4,702,245 A | 10/1987 | Schroder et al. | |
| 4,754,328 A | 6/1988 | Barath et al. | |
| 4,765,313 A | 8/1988 | Kumakura | |
| 4,790,295 A | 12/1988 | Tashiro | |
| 4,807,594 A | 2/1989 | Chatenever | |
| 4,807,598 A | 2/1989 | Hasegawa | |
| 4,830,460 A | 5/1989 | Goldenberg | |
| 4,834,070 A | 5/1989 | Saitou | |
| 4,837,857 A | 6/1989 | Scheller et al. | |
| 4,856,495 A | 8/1989 | Tohjoh et al. | |
| 4,867,137 A | 9/1989 | Takahashi | |
| 4,896,941 A | 1/1990 | Hayashi et al. | |
| 4,948,894 A | 8/1990 | Moran et al. | |
| 4,965,960 A | 10/1990 | Moore | |
| 4,984,563 A | 1/1991 | Renaud | |
| 5,116,317 A | 5/1992 | Carson et al. | |
| 5,121,740 A * | 6/1992 | Uram | A61F 9/008 600/108 |
| 5,323,766 A | 6/1994 | Uram | |
| 5,409,480 A | 4/1995 | Uram | |
| 5,419,312 A | 5/1995 | Arenberg et al. | |
| 5,443,057 A | 8/1995 | Elmore | |
| 5,608,835 A | 3/1997 | Ono et al. | |
| 5,643,250 A | 7/1997 | O'Donnell | |
| 5,738,676 A | 4/1998 | Hammer | |
| 5,788,628 A | 8/1998 | Matsuno et al. | |
| 5,807,242 A | 9/1998 | Scheller et al. | |
| 5,810,713 A | 9/1998 | Rondeau et al. | |
| 5,865,831 A | 2/1999 | Cozean et al. | |
| 5,868,665 A * | 2/1999 | Biggs | A61B 1/00128 600/112 |
| 5,893,828 A | 4/1999 | Uram | |
| 5,983,749 A | 11/1999 | Holtorf | |
| 6,080,101 A | 6/2000 | Yutsuno et al. | |
| 6,179,829 B1 | 1/2001 | Bisch et al. | |
| 6,193,650 B1 | 2/2001 | Ryan | |
| 6,260,434 B1 | 7/2001 | Holtorf | |
| 6,355,027 B1 | 3/2002 | Le et al. | |
| 6,360,630 B2 | 3/2002 | Holtorf | |
| 6,368,269 B1 | 4/2002 | Lane | |
| 6,419,627 B1 | 7/2002 | Nun | |
| 6,451,005 B1 | 9/2002 | Saitou et al. | |
| 6,452,123 B1 | 9/2002 | Chen | |
| 6,572,536 B1 | 6/2003 | Bon et al. | |
| 6,639,332 B2 | 10/2003 | Metzler et al. | |
| 6,689,975 B2 | 2/2004 | Metzler et al. | |
| 6,862,951 B2 | 3/2005 | Peterson et al. | |
| 6,997,868 B1 | 2/2006 | Uram | |
| 7,012,203 B2 | 3/2006 | Hanson et al. | |
| 7,189,226 B2 | 3/2007 | Auld et al. | |
| 7,289,139 B2 | 10/2007 | Amling et al. | |
| 7,404,794 B2 | 7/2008 | Scholly | |
| 7,435,218 B2 | 10/2008 | Krattiger | |
| 7,439,463 B2 | 10/2008 | Brenner et al. | |
| 7,470,277 B2 | 12/2008 | Finlay et al. | |
| 7,522,797 B2 | 4/2009 | Treado et al. | |
| 7,626,132 B2 | 12/2009 | Mezhinsky | |
| 7,781,941 B2 | 8/2010 | Horvath et al. | |
| 7,845,537 B2 | 12/2010 | Shelton et al. | |
| 7,846,150 B2 | 12/2010 | Hamel et al. | |
| 7,901,351 B2 | 3/2011 | Prescott | |
| 7,942,814 B2 | 5/2011 | Remijan et al. | |
| 7,972,326 B2 | 7/2011 | Scheller | |
| 8,029,499 B2 | 10/2011 | Zimare et al. | |
| 8,038,602 B2 | 10/2011 | Gill et al. | |
| 8,048,094 B2 | 11/2011 | Finlay et al. | |
| 8,159,370 B2 | 4/2012 | Schields et al. | |
| 8,194,122 B2 | 6/2012 | Amling et al. | |
| 8,323,181 B2 | 12/2012 | Mukherjee et al. | |
| 8,348,924 B2 | 1/2013 | Christian et al. | |
| 8,545,396 B2 | 10/2013 | Cover et al. | |
| 8,599,250 B2 | 12/2013 | Amling et al. | |
| 8,647,333 B2 | 2/2014 | Mansour | |
| 8,666,479 B2 | 3/2014 | Berndt | |
| 8,680,412 B2 | 3/2014 | Horvath et al. | |
| 8,749,188 B2 | 6/2014 | Tran et al. | |
| 2003/0036680 A1 | 2/2003 | Black | |
| 2005/0033309 A1 | 2/2005 | Ryan | |
| 2005/0113641 A1 | 5/2005 | Bala | |
| 2005/0192480 A1 * | 9/2005 | Toriya | A61B 90/30 600/182 |
| 2006/0025655 A1 | 2/2006 | Uram | |
| 2006/0084952 A1 | 4/2006 | Pallikaris et al. | |
| 2006/0276690 A1 | 12/2006 | Farris et al. | |
| 2007/0135806 A1 | 6/2007 | Easley | |
| 2007/0139924 A1 | 6/2007 | Easley et al. | |
| 2007/0139950 A1 | 6/2007 | Easley et al. | |
| 2007/0166661 A1 | 7/2007 | Lint et al. | |
| 2007/0213586 A1 | 9/2007 | Hirose et al. | |
| 2007/0293727 A1 | 12/2007 | Goldfarb et al. | |
| 2008/0071143 A1 | 3/2008 | Gattani et al. | |
| 2008/0108981 A1 * | 5/2008 | Telfair | A61B 18/24 606/4 |
| 2008/0114387 A1 | 5/2008 | Hertweck et al. | |
| 2008/0140158 A1 | 6/2008 | Hamel et al. | |
| 2008/0150754 A1 | 6/2008 | Quendt | |
| 2009/0118715 A1 * | 5/2009 | Mansour | A61F 9/008 606/4 |
| 2009/0259098 A1 | 10/2009 | Krattiger | |
| 2010/0198200 A1 | 8/2010 | Horvath | |
| 2010/0204609 A1 | 8/2010 | Worth et al. | |
| 2010/0318074 A1 | 12/2010 | Dacquay et al. | |
| 2011/0282139 A1 | 11/2011 | Uram | |
| 2012/0083800 A1 | 4/2012 | Andersohn | |
| 2012/0191078 A1 | 7/2012 | Yadlowsky | |
| 2012/0203075 A1 | 8/2012 | Horvath et al. | |
| 2013/0324794 A1 | 12/2013 | Cover et al. | |
| 2014/0066723 A1 | 3/2014 | Horvath et al. | |
| 2014/0121653 A1 | 5/2014 | Abe et al. | |

FOREIGN PATENT DOCUMENTS

| | | |
|---|---|---|
| EP | 1512366 A1 | 3/2005 |
| JP | 6-80401 U | 11/1994 |
| JP | 2001218851 A | 8/2001 |
| JP | 200416317 A | 1/2004 |

(56) References Cited

FOREIGN PATENT DOCUMENTS

| JP | 2005532139 A | 10/2005 |
| JP | 2006223710 A | 8/2006 |
| WO | 9849929 A1 | 11/1998 |
| WO | 2008-108425 A1 | 12/2008 |

OTHER PUBLICATIONS

Laredo et al., Percutaneous Biopsy of Osteoid Osteomas Prior to Percutaneous Treatment Using Two Different Biopsy Needles, Cardiovasc Intervent Radiol (2009) 32:998-1003.

* cited by examiner

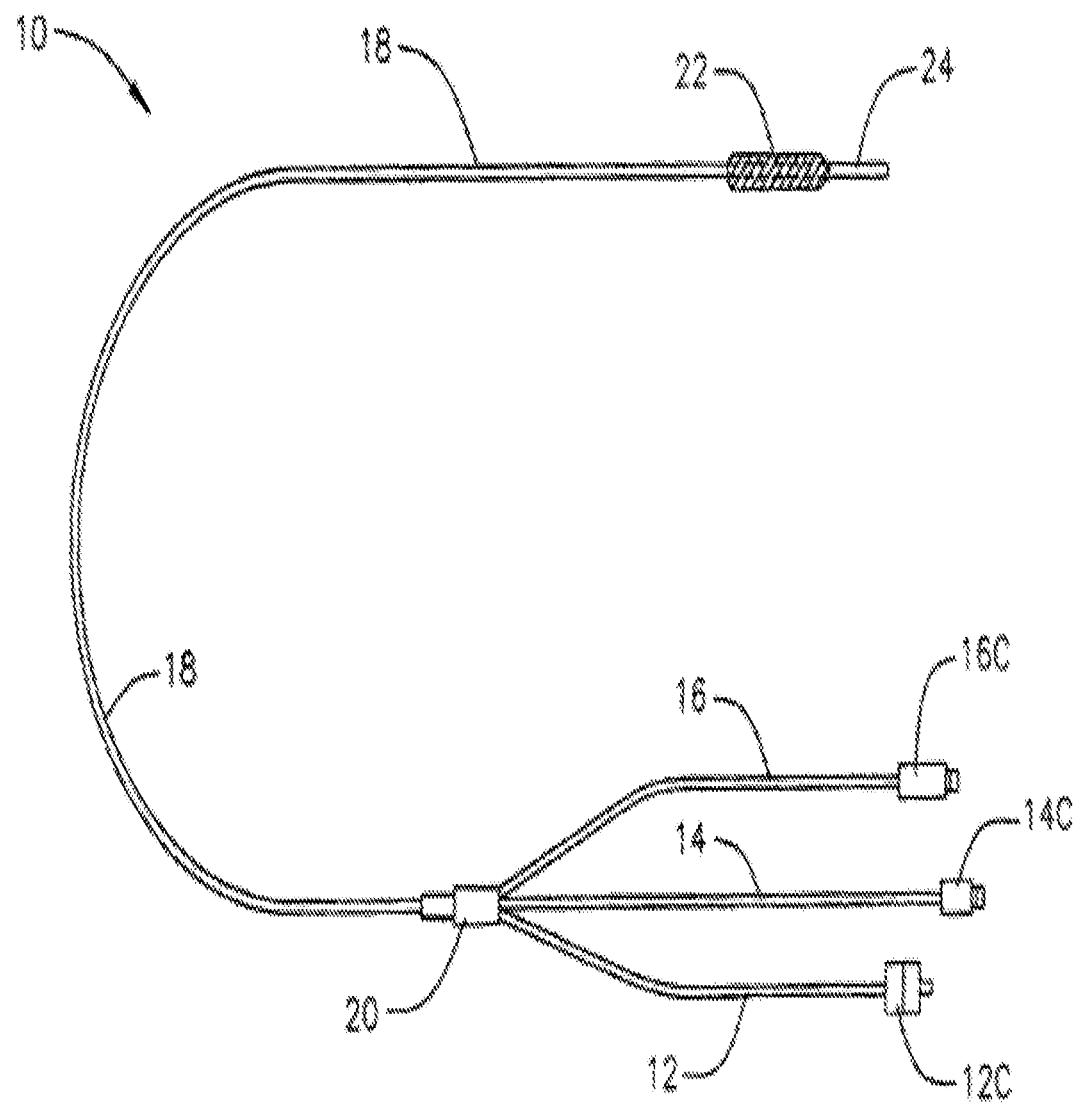
CONVENTIONAL
FIG. 1

TOP

SIDE

REAR

LASER VIDEO ENDOSCOPE

CROSS-REFERENCES TO RELATED APPLICATIONS

This application is a continuation of U.S. patent application Ser. No. 14/966,151, filed Dec. 11, 2015, now pending, which is a continuation-in-part of U.S. patent application Ser. No. 13/084,789, filed on Apr. 12, 2011, now abandoned, and is a continuation-in-part of U.S. patent application Ser. No. 13/314,371, filed on Dec. 8, 2011, now U.S. Pat. No. 10,226,167, which is a continuation-in-part of U.S. patent application Ser. No. 12/779,214, filed on May 13, 2010, now abandoned, the entire disclosures of which are hereby incorporated by reference.

Other prior applications are U.S. Pat. No. 5,121,740 issued on Jun. 16, 1992 and U.S. Pat. No. 6,997,868 issued on Feb. 14, 2006, the entire disclosures of which are incorporated herein by reference.

BACKGROUND OF THE INVENTION

This invention relates in general to a medical laser video endoscope and more particularly to one in which the operating probe can be economically disposed of after each use and/or can have a relatively small gage size.

Laser video endoscopes are used in glaucoma, retinal and vitrectomy operations, and some conventional endoscopes can be reused after autoclaving or other sterilization. Reuse occurs in large part because of the expense of the endoscope. The most significant expense factor is the image guide which has a large number of micron size optical fibers. For example, for an endoscope employing 17,000 fibers to provide a 17,000 pixel image (a 17k endoscope) image guide alone can cost about $340.00, while the price of a fully assemble 17k endoscope can be in the $2,000 range. This is a major incentive for the re-use of the endoscope after sterilization rather than disposing of the endoscope after each procedure.

The expense factor means that as a practical matter the endoscope will be reused after sterilization rather than disposed of. However, there is greater security from infection if the probe of the endoscope can be disposed of after each usage instead of being subject to the possibilities of human error in the sterilization process.

Another feature of conventional endoscopes is employing a probe passing through a 20 gauge tissue incision during ophthalmological surgery. A 20 gauge incision has been a standard in the art of ophthalmological surgery and is used for entry by instruments employed during an ophthalmological surgical routine.

However, a smaller 23 gauge sleeve has been employed more recently. This sleeve, such as a trocar sleeve is a tube implanted in a body wall which permits insertion and removal of a surgical instrument without touching the body wall tissue. The value of the 23 gauge sleeve is that it involves a smaller incision and therefore quicker recovery time. The 23 gauge sleeve provides an opening smaller than the 20 gauge incision and thus requires the probes thereof to be smaller in diameter so that they can fit through the 23 gauge sleeve.

One problem is that a 23 gauge probe is so small in diameter (25 mils, or 0.635 mm) that it is fragile and tends to break. Most breakage occurs at the juncture between the hand piece and the probe. This breakage problem becomes a major concern when using a laser video endoscope because of the cost of these endoscopes.

SUMMARY OF THE INVENTION

Exemplary embodiments of the present invention address at least some of the drawbacks of conventional endoscopes by providing endoscope designs for which the cost is reasonable enough to permit and encourage disposal of the probe after each use rather than have recourse to sterilization.

Also, exemplary embodiments of the present invention address at least some of the drawbacks of conventional endoscopes by providing endoscope designs which include a probe that can be inserted through, for example, a 23 gauge sleeve and can maintain sufficient robustness so as to minimize the amount of breaking.

Exemplary embodiments of the present invention provide endoscope designs, which permit disposal of the probe after each use and/or include a probe that can be inserted through, for example, a 23 gauge sleeve, while maintaining a probe look and feel familiar to surgeons and including operating characteristics of imaging, illumination, and laser oblation.

According to an exemplary embodiment of the present invention, a laser video endoscope comprises a laser guide, an illumination guide and an image guide, which can be fiber optical guides extending through a probe portions of the endoscope and through a hand piece that supports the probe portion which can protrude from the distal end of the hand piece.

According to an exemplary implementation of the embodiments of the present invention, the hand piece includes one or more channels having a distal end at the distal end of the hand piece. The one or more channels can be configured to accommodate at least one of the laser guide, an illumination guide and/or an image guide extending from the probe portion into the hand piece.

According to another exemplary implementation of the embodiments of the present invention, the hand piece includes a first channel having a distal end at the distal end of the hand piece such that an illumination guide and a laser guide can continue to extend from the probe portion to an illumination source and a laser energy source, respectively, via the first channel of the hand piece and through a relatively long flexible optical fiber cable connected to the hand piece at a proximal end of the first channel.

According to yet another exemplary implementation of the embodiments of the present invention, the hand piece includes a second channel having a distal end at the distal end of the hand piece such that an optical image guide extends from the probe portion through the second channel of the hand piece and ends at a proximal end of a second channel.

According to yet further exemplary implementation of the embodiments of the present invention, the proximal end of the second channel is at the proximal end of the hand piece, and the proximal end of the hand piece is configured for removable attachment to a camera assembly such that the camera assembly can be optically coupled to the end of the optical fiber image guide.

Exemplary embodiments of the present invention provide an endoscope system comprising: a laser video endoscope including a hand piece supporting a probe, with a laser guide, an illumination guide and an image guide extending through the probe and the hand piece; and a camera assembly, which can be removably attached directly to the hand piece and has an input optically coupled to an end of the image guide extending though the hand piece.

According to still further exemplary implementation of the embodiments of the present invention, the camera assembly includes an output having an electrical cable extended from the camera assembly to transmit an electrical image signal from the camera assembly to an image processor, an image display device, or any site where an image can be provided for the surgery.

According to still further exemplary implementation of the embodiments of the present invention, camera assembly and its electrical cable can be uncoupled from the hand piece and reused in a plurality of endoscopic routines, while the laser video endoscope including the probe portion and the hand piece can be disposed of after each medical routine thereby providing assurance of an antiseptic procedure.

Exemplary embodiments of the present invention provide laser video endo scopes for use in ophthalmology operations, the endoscopes including a probe portion which, for example, can be passed through a 23 gauge sleeve, such as a trocar sleeve.

According to an exemplary implementation of the embodiments of the present invention, a laser video endoscope includes a, for example stainless steel, probe having a distal portion and a proximal portion, such that the proximal portion extends from the distal end of a hand piece of the laser video endoscope, and the outside diameter (OD) of the proximal portion as measured at least near the distal end of the hand piece is greater than the OD of the distal portion.

According to another exemplary implementation of the embodiments of the present invention, the distal portion has an OD less than 25 mils (thousandths of an inch), or about 0.64 mm, and about 2 mils, or 0.05 mm, wall thickness, such that at least the distal portion of the probe can be inserted through a 23 gauge sleeve.

According to yet another exemplary implementation of the embodiments of the present invention, the proximal portion of the probe, exiting from the hand piece, has an OD of about 31 mils, or 0.79 mm, and about 5 mil, or 0.13 mm, wall thickness.

According to yet further exemplary implementation of the embodiments of the present invention, the distal portion has a length of about 710 mils, or 18 mm, at OD of less than about 25 mils, or 0.64 mm.

According to yet another exemplary implementation of the embodiments of the present invention, a distal portion of a probe of a laser video endoscope includes: a laser guide comprising a laser fiber disposed within the inner diameter of the distal portion of the probe; an image guide comprising an image bundle, which has a plurality of fibers arranged in an essentially circular configuration, disposed within the inner diameter of the distal portion of the probe not occupied by the laser fiber; and an illumination guide comprising an illumination bundle, which has a plurality of fibers filling the remaining of the inner diameter of the distal portion of the probe not occupied by the laser fiber and the image bundle.

According to still further exemplary implementation of the embodiments of the present invention, the inner diameter of the distal portion of the probe is about 21 mils, or 0.54 mm, the laser fiber of the laser guide has an OD of about 100 microns, or 0.1 mm, the image bundle of the image guide has about 6,000 fibers arranged in an essentially circular configuration having an OD of about 14 mils, or 0.36 mm, and the illumination bundle of the illumination guide has about 210 fibers filling the remaining 21 mils, or 0.54 mm, inner diameter of the distal portion of the probe not occupied by the laser fiber and the image bundle.

Exemplary embodiments of the present invention provide endoscope designs where a laser fiber can selectively accommodate input from laser energy sources having different wavelengths, such as for example a green laser having a wavelength of 532 nanometers.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 1 is a schematic illustration of a conventional endoscope design.

DETAILED DESCRIPTION OF EXEMPLARY EMBODIMENTS

Figure 2:
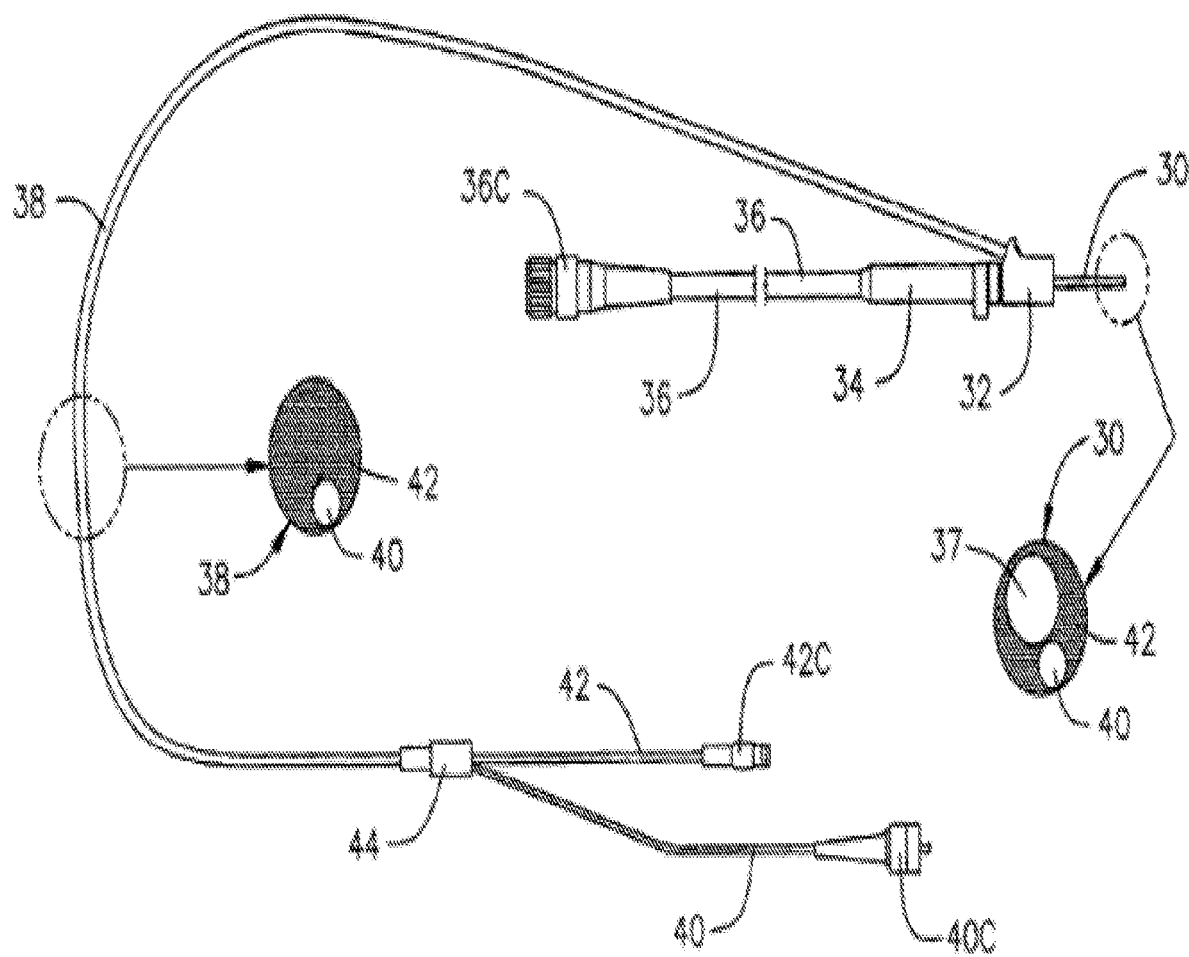
FIG. 2 is a schematic illustration of an endoscope system according to an exemplary embodiment of the present invention.
Figure 3:
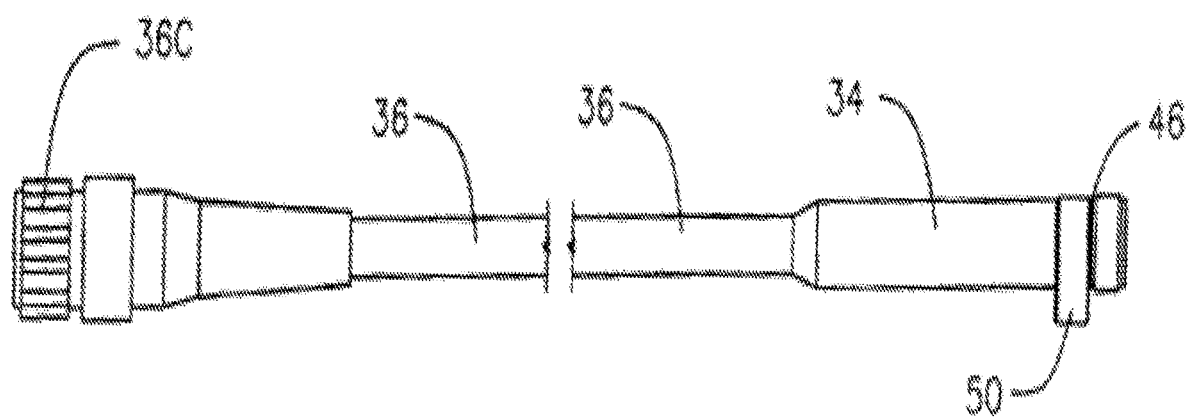
FIG. 3 is a longitudinal view of a camera assembly of an endoscope system according to an exemplary embodiment of the present invention.
Figure 4:
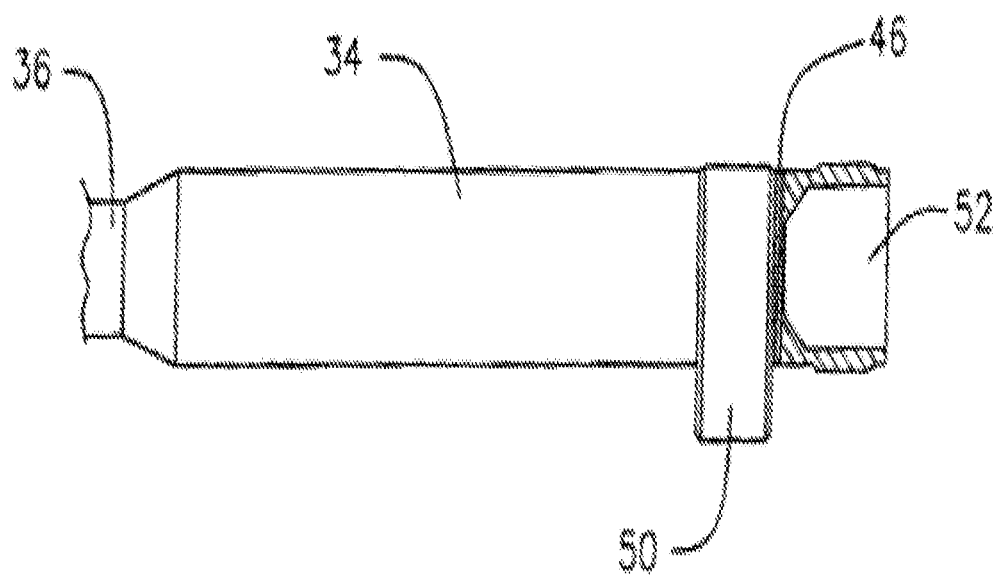
FIG. 4 is a partial longitudinal sectional view of a camera assembly including exemplary implementation of camera assembly components according to an exemplary embodiment of the present invention.

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention. Also, well-known functions or constructions are omitted for clarity and conciseness. Certain exemplary embodiments of the present invention may be described below in the context of commercial application. Such exemplary implementations are not intended to limit the scope of the present invention, which is defined in the appended claims.

It is to be noted that, while descriptive terms such as "hand piece", "probe", and "fiber" are used throughout this specification, it is not intended to limit components that can be used in combinations or individually to implement various aspects of the embodiments of the present invention.

Referring now to the drawings, wherein like reference numerals designate identical or corresponding parts throughout the several views, embodiments of the present invention are shown in schematic detail.

FIG. 1 illustrates a configuration of a conventional laser video endoscope 10 having an operating probe 24, a hand piece 22, and a cable 18 which carries a laser guide 12, an illumination guide 14 and an image guide 16. These are all fiber optic guides which extend from the distal end of the probe 24 to the terminals 12C, 14C and 16C, respectively. Distal of the trifurcation zone 20, the fiber optic guides are combined geometrically to provide a minimum diameter cable.

Referring to FIGS. 2 through 6, a laser video endoscope according to an exemplary embodiment of the present invention includes a hand piece 32, a probe 30 extending from the distal end of the hand piece 32, and a camera assembly 34 removably coupled to the proximal end of the hand piece 32. In an exemplary implementation of the present invention, the camera assembly 34 is directly connected to the proximal end of the hand piece 32 through engagement of a nose 54 of the hand piece 32 and recess 52 of the camera assembly 34. While probe 30 is illustrated as an essentially straight, other probes, such as curved probes can be interchangeably used without departing from the scope of the exemplary embodiments of the present invention described herein.

As illustrated in FIG. 2, according to exemplary embodiments of the present invention a laser guide comprising fiber 40, an illumination guide comprising fibers 42, and an image guide comprising fibers 35 extend form distal end of probe 30 into hand piece 32. The proximal end of probe 30 can be fixedly attached to distal end of hand piece 32, for example by being cemented together by a known process.

Figure 5A:
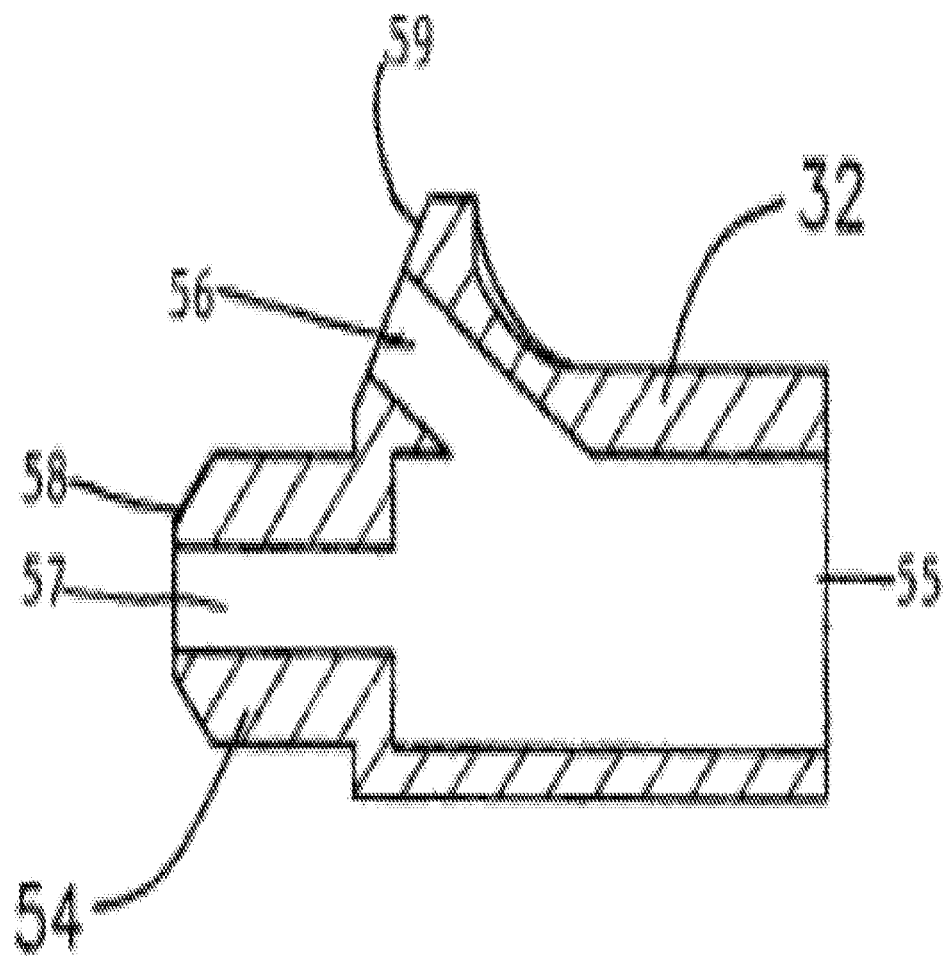
FIG. 5A and FIG. 5B are sectional views of a hand piece of an endoscope according to an exemplary embodiment of the present invention.
Figure 5B:
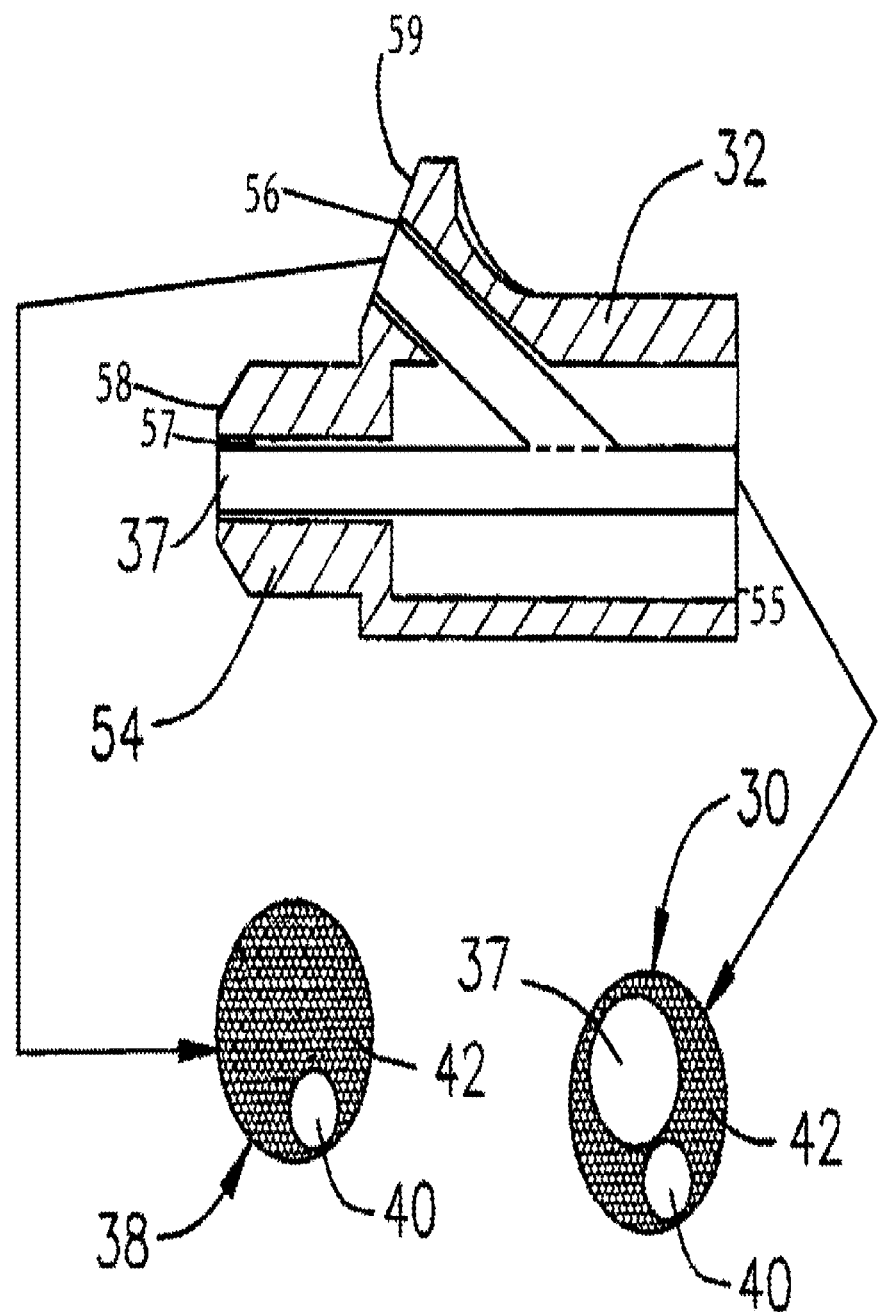
Figure 6:
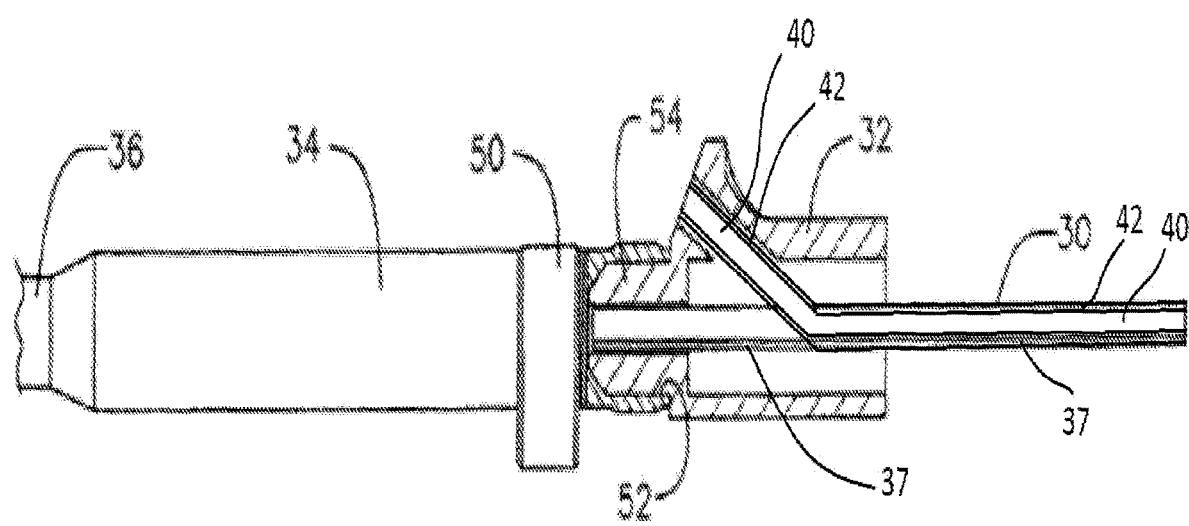
FIG. 6 is a schematic illustration of an endoscope system, including a probe, a hand piece, and a camera assembly, according to an exemplary embodiment of the present invention.

As further illustrated in FIG. 2, FIG. 5A and FIG. 5B, according to an exemplary implementation of embodiments of the present invention, the hand piece 32 contains channels 55, 56 and 57. In an exemplary implementation, the hand piece 32 separates the image guide fibers 37, laser guide fiber 40, and illumination guide fibers 42 entering channel 55 at the distal end of hand piece 32 from the proximal end of probe 30, such that only image guide fibers 37 extend through channel 57, while the laser guide fiber 40 and the illumination guide fibers 42 extend through channel 56. Channel 57 terminates at surface 58 at the proximal end of hand piece 32 and is used to optically couple the image guide fibers 37 extending from distal end of probe 30 to the lens or input optics of the camera assembly 4. Channel 56 terminates at hand piece surface 59 and is used to accommodate the laser guide fiber 40 and the illumination guide fibers 42 extending from the distal end of probe 30 to be carried proximately by the cable 38. In an exemplary implementation, channels 56 and 57 extend from channel 55 at a non-zero angle with respect to each other, as shown in the example of FIG. 5A where channels 56 and 15 extend (or meet) at an angle.

In an exemplary implementation of embodiments of the present invention, image guide fibers 37 which extend through the probe 30 and hand piece 32 carry the image and can be removably coupled directly to the optics of the camera assembly 34. In an exemplary implementation of the embodiments of the present invention as illustrated in FIGS. 4, 5A, 5B, and 6, the distal end of the camera assembly 34 has a recess 52 which removably engages a nose 54 of the hand piece 32. Positioning of the camera assembly 34 at the hand piece 32 can permit a standard optical coupling of the image output at the proximal end of the optical image guide fibers 37 to the optics of camera assembly 34.

In an exemplary implementation of embodiments of the present invention, camera assembly 34 can provide an electrical image that is transmitted proximally along the electrical cable 36 connected at the output of camera assembly 34. The camera may be any one of a number of known types, which include for example optical and/or image processing elements, and may be specially designed to fit the geometry of the camera assembly to ensure usable image input from image guide fibers 37 at the proximal end of hand piece 32.

In an exemplary implementation of embodiments of the present invention, an optical guide cable 38 extends in the proximal direction from the hand piece 32 and carries the laser guide fiber 40 and the illumination guide fibers 42 for conveying the laser energy and the illumination energy, respectively, to the probe 30. In a further exemplary implementation of embodiments of the present invention, cable 38 extends in the proximal direction to a bifurcation junction 44 where the laser guide fiber 40 and illumination guide fibers 42 are separated and terminated at terminals 40C and 42C for connection to sources of laser energy and illumination energy, respectively. In yet further exemplary implementation of embodiments of the present invention, image carrying electrical cable 36 terminating at terminal 36C can be about as long as the optical guide cable 38, and each cable 36 and 38 can be as long as required for an installation.

According to exemplary embodiments of the resent invention, it becomes possible to terminate image guide fibers 37 at the proximal end of hand piece 32 due to direct optical coupling of image guide fibers 37 to the optics of camera assembly 34 as provided by hand piece 32. The camera assembly 34 can be uncoupled from the hand piece 32 so that the relatively expensive camera assembly can be reused. Also, by positioning the camera assembly 34 at the hand piece 32, the lengthy and expensive optical image guide proximal of the hand piece 32 is avoided.

Thus, laser video endoscopes according to exemplary embodiments of the present invention can eliminate the conventional costly and lengthy image fibers such as those extending from the hand piece 22 to terminal 16C as shown in FIG. 1. Instead, in laser video endoscopes according to exemplary embodiments of the present invention, the image can be carried to terminal 36C in an electric cable 36 proximally of the camera assembly 34 coupled directly to hand piece 32. For example, a relatively long electrical cable 36 can extend from proximal end of camera assembly 34 to a terminal 36C which is coupled to an appropriate image processing or display mechanism, for example a video screen so that the operating surgeon can view the image during the course of manipulating the probe 30.

This combination of reuse of the camera assembly 34 and elimination of an extensive length of expensive fiber optic image guide means that disposability of the probe 30 is economically acceptable even though the hand piece 32 and the laser guide fiber 40 and illumination guide fibers 42 in the cable 38 are also disposed of after each medical routine.

In an exemplary implementation, camera assembly 34 can include a laser filter 46 for example to protect the camera film from laser energy and to permit the surgeon to observe the operation when laser pulses are firing. In yet further exemplary implementation, a filter for multiple wavelength lasers can be present, such that for example 810 nm and 532 nm laser can be used.

In another exemplary implementation of embodiments of the present invention, camera assembly 34 can include a manually operated spring latch (not shown) to facilitate readily mounting the camera assembly 34 to the hand piece 32 and readily removing the camera assembly 34 from the hand piece 32.

In yet another exemplary implementation, the camera assembly 34 can include a focus ring 50 to assure adequate focus of the image provided onto the image receptors of the camera assembly 34 positioned at the proximal end of image guide fibers 37 which extends from the distal end of the probe 30 and through channels 55 and 57 of the hand piece 32.

A variant on exemplary embodiments of the present invention as illustrated for example in FIGS. 2 through 6 is an arrangement in which the uncoupling at the proximal end of the hand piece 32 will uncouple not only the camera assembly 34 at surface 58, but also the cable 38, for example at or near surface 59, so that only the probe 30 and the hand piece 32 would be disposed of between each operation.

In the exemplary implementations of FIGS. 1 through 6, the image guide 37 within the probe 30 and hand piece 32 can be a fiber optic bundle; however, other exemplary configurations can provide an image guide function, such as for example a gradient index lens, often referred to as a GRIN lens.

Figure 7:
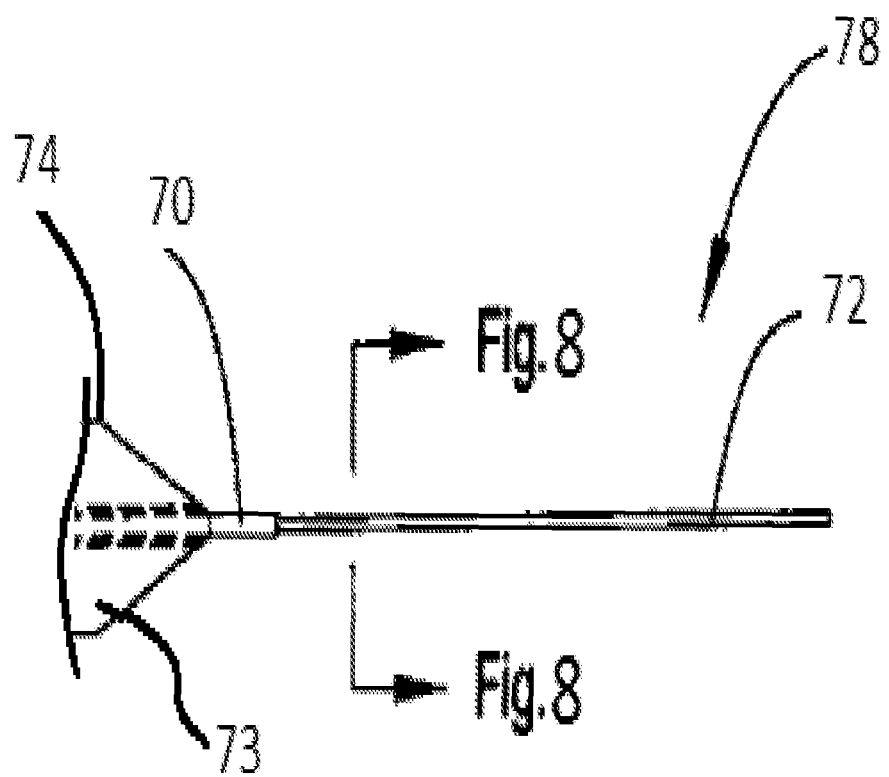
FIG. 7 is an illustration of a distal end of a hand piece and a probe according to an exemplary embodiment the present invention.
Figure 8:
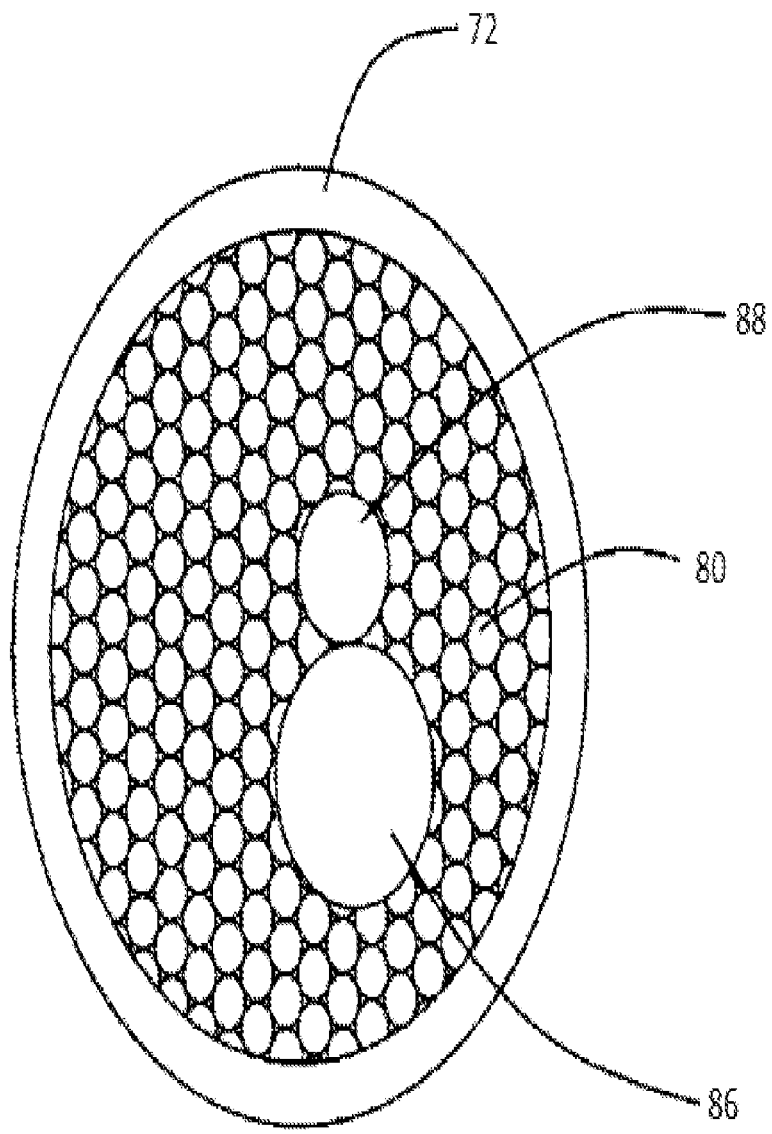
FIG. 8 is a cross sectional view of a distal portion of the probe of an exemplary embodiment illustrated in FIG. 7.
Figure 9A:
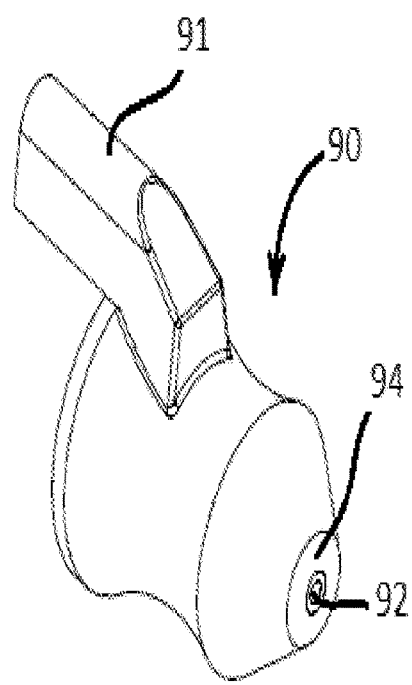
FIGS. 9A, 9B, 9C and 9D are multiple views illustrating a distal portion of a hand piece according to an exemplary embodiment of the present invention.
Figure 9B:
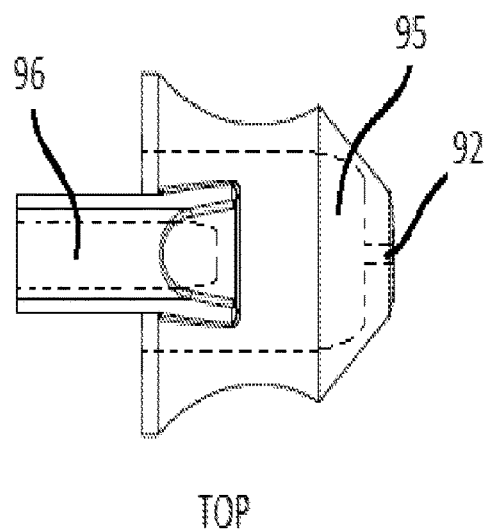
Figure 9C:
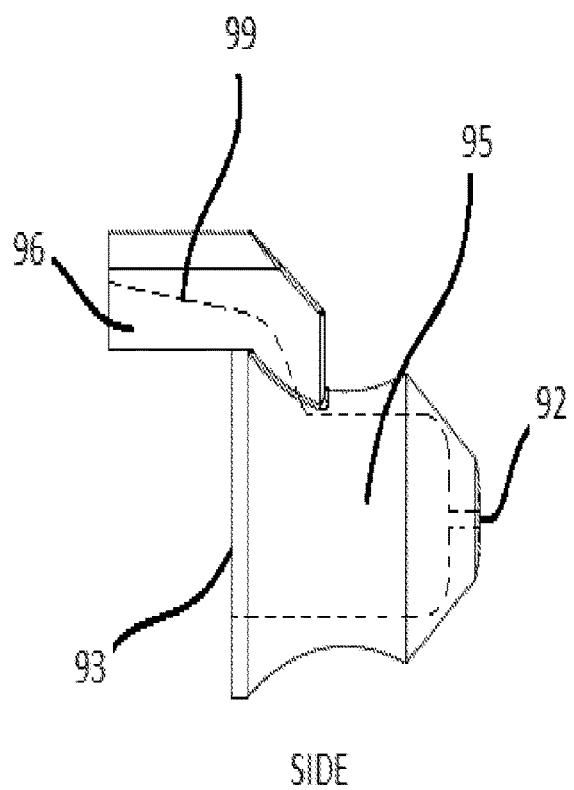
Figure 9D:
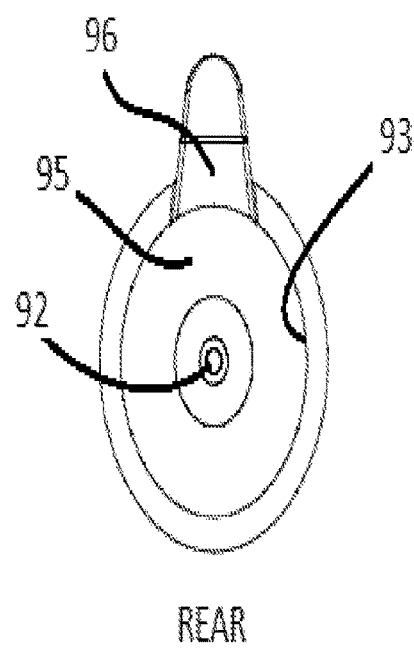
Figure 10A:
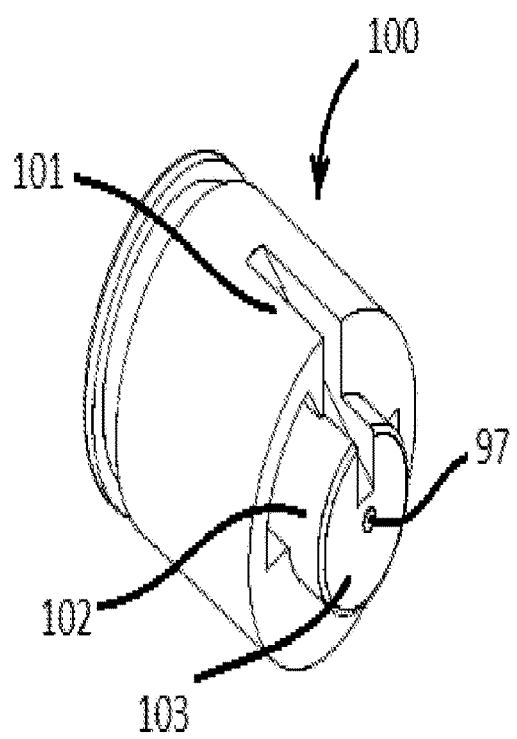
FIGS. 10A, 10B, 10C and 10D are multiple views illustrating a proximal portion of a hand piece according to an exemplary embodiment of the present invention.
Figure 10B:
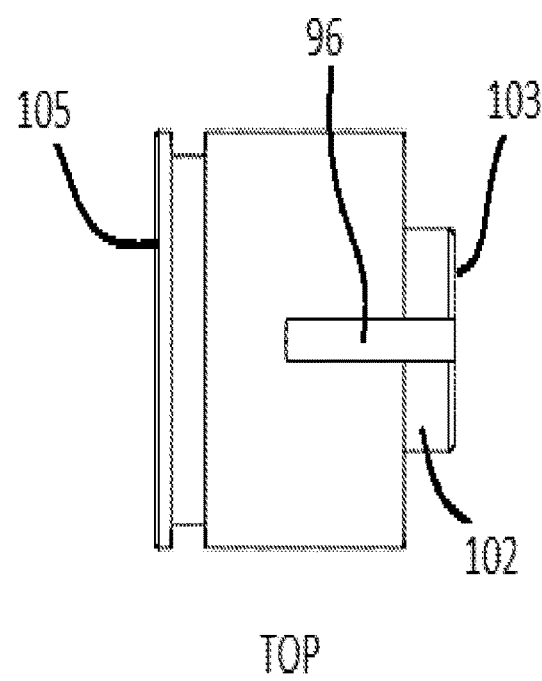
Figure 10C:
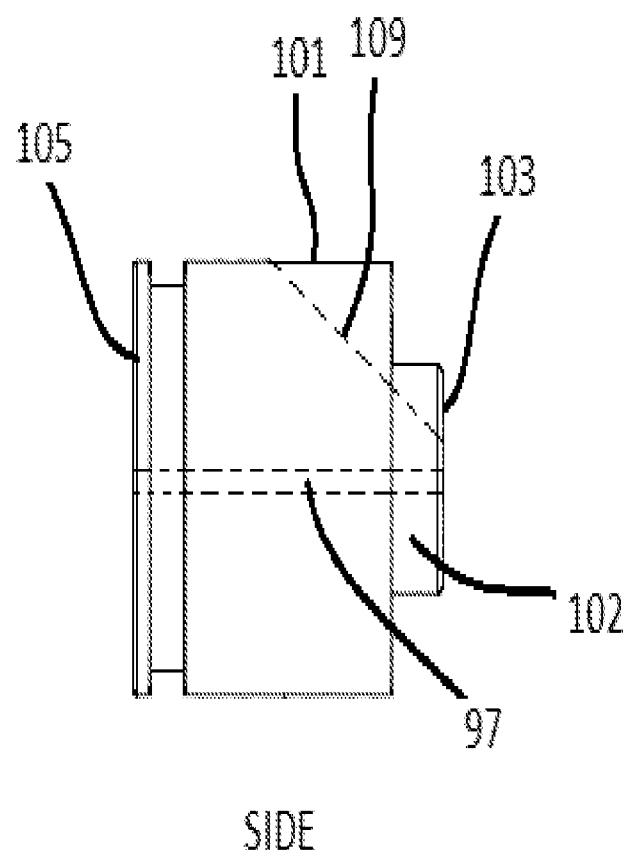
Figure 10D:
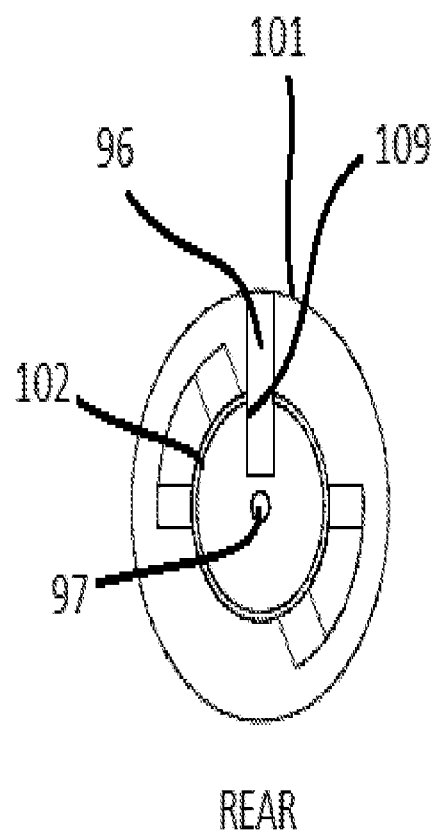

Referring to FIG. 7 and FIG. 8, a laser video endoscope according to an exemplary embodiment of the present invention includes a probe 78, and a hand piece 74 (partially illustrated). The probe 78 has a proximal portion 70 and a distal portion 72 such that the proximal portion 70 extends from the distal end 73 of hand piece 74 of the laser video endoscope, and the outside diameter (OD) of the proximal portion 70 as measured at least near the distal end 73 of hand piece 74 is greater than the OD of the distal portion 72.

Referring to FIG. 8, a cross sectional view of distal portion 72 of probe 78 according to an exemplary implementation of the embodiments of the present invention illustrates a configuration of image guide comprising fibers 86, laser guide comprising fiber 88, and illumination guide comprising fibers 80 within probe 78. As shown in FIG. 8, image guide 86 and laser guide 88 are arranged such that OD of fibers of image guide 86 and OD of fiber of laser guide 88 do not intersect or overlap at any cross section of distal portion 72 of probe 78. As further shown in FIG. 8, according to an exemplary implementation of the embodiments of the present invention, fibers of illumination guide 80 fill the remaining volume of distal portion 72 of probe 78 such that OD of fibers of image guide 86 and OD of fiber of laser guide 88 do not intersect or overlap OD of any fiber of illumination guide 80 at any cross section of distal portion 72 of probe 78.

In an exemplary implementation of the embodiments of the present invention, the proximal portion 70 can have between about 20 and 22 gauge (35 and 31 mils, or 0.89 and 0.79 mm) outer diameter and about a 5 mil, or 0.13 mm, wall thickness. The probe can be stainless steel. The proximal portion 70 extends into the hand piece 74. Thus, at the juncture of the end of the hand piece 74 and the probe 78, there is a diameter having sufficient robustness to contribute to minimizing the likelihood of breaking at the juncture between distal end 73 of hand piece 74 and the proximal end of probe 78.

In an exemplary implementation of the embodiments of the present invention, the length of the proximal portion 70 of the probe 78 can be about 120 mils, or 3 mm, and the length of the distal portion 72 can be about 710 mils, or 18 mm, for a probe 78 length of about 830 mils, or 21 mm.

In an exemplary implementation of the embodiments of the present invention, the distal portion 72 of the probe 78 can have OD of about 25 mils, or 0.64 mm, or less, and can extend through a 23 gauge sleeve to provide illumination and laser energy delivery within the eye during a surgical procedure and to transmit image from the eye. This distal portion 72 can have a wall thickness of about 2 mils, or 0.05 mm, and a length of about 710 mils, or 18 mm. The 710 mil, or 18 mm, length is long enough for most applications and short enough to minimize breaking.

While it has been found that exemplary length described herein for distal portion 72 contributes to the robustness of probe 78, the dimensional values can be varied slightly to provide a probe that can be used with other small size sleeves.

Probe 78 having OD of about 25 mil, or 0.64 mm, according to exemplary embodiments of the present invention can meet the need of providing enough light and enough laser energy while maintaining an adequate image guide by providing trade-off of dimensions for each of respective fibers transmitting illumination light, laser energy, and images as follows.

In the example of FIG. 8, image guide 86 comprises a bundle of about 6,000 fibers arranged in an essentially circular cross-sectional configuration with OD of about 14 mils, or 0.36 mm, and laser guide 88 comprises a fiber with OD of about a 100 micron, or 0.1 mm. Image guide 86 and laser guide 88 are contained within the distal portion 72 of the probe 78 having OD of approximately 25 mils, or 0.64 mm, wall thickness of approximately 2 mils, or 0.05 mm, and an inner diameter of approximately 21 mils, or 0.54 mm, with fibers of illumination guide 80 filling the remaining volume of distal portion 72 of probe 78.

According to exemplary embodiments of the present invention, probe 78 can be made robust enough to minimize breakage by a combination of: (a) rigid construction for probe 78 wall, (b) two-diameter design for proximal portion 70 and distal portion 72 and (c) limited length for distal portion 72. A particularly advantageous configuration according to an exemplary implementation of probe 78 includes a combination of: (a) probe 78 having a metallic wall, (b) proximal portion 70 having OD of 35 mil and wall thickness of 5 mils that extends through the hand piece 74, and distal portion 72 having OD of 25 mil and wall thickness of 2 mils, and (c) distal portion 72 having a length of no more than 710 mils.

It has been found that such a design according to exemplary embodiments of the present invention as illustrated in FIGS. 7 and 8 can provides sufficient illumination to illuminate a 90 degree field. One of the compromises made in order to get a small diameter probe is to reduce the laser guide 88 fiber diameter from 200 microns to 100 microns. In an exemplary implementation, a 532 nanometer (nm) laser source, or a green laser, can be advantageously provide a desirable laser energy. For example, output of a 532 nm laser is more coherent and less divergent than the 810 nm laser. Accordingly, in an exemplary implementation of the present invention, the use of a 532 nm laser in combination with the reduced size of the laser fiber 88 provides a reasonable amount of laser energy for the ophthalmological operations involved.

In yet another exemplary implementation of the embodiments of the present invention, the illumination guide 80 can be reduced from approximately 220 fibers to about 70 fibers thereby materially contributing to a smaller diameter of probe 78.

Exemplary embodiments of the present invention have been described in connection with an implementation that permits use with a 23 gauge sleeve. It should be understood that variations could be made to adapt the design described to use with sleeves having variations on the 23 gauge or to be used without a sleeve. The exemplary embodiments of the present invention describe combinations of a number of features and trade-offs designed to work together to provide an operable and useful laser video endoscope having a small probe that provides access for eye operations with minimum trauma and reduced healing time.

Figure 11:
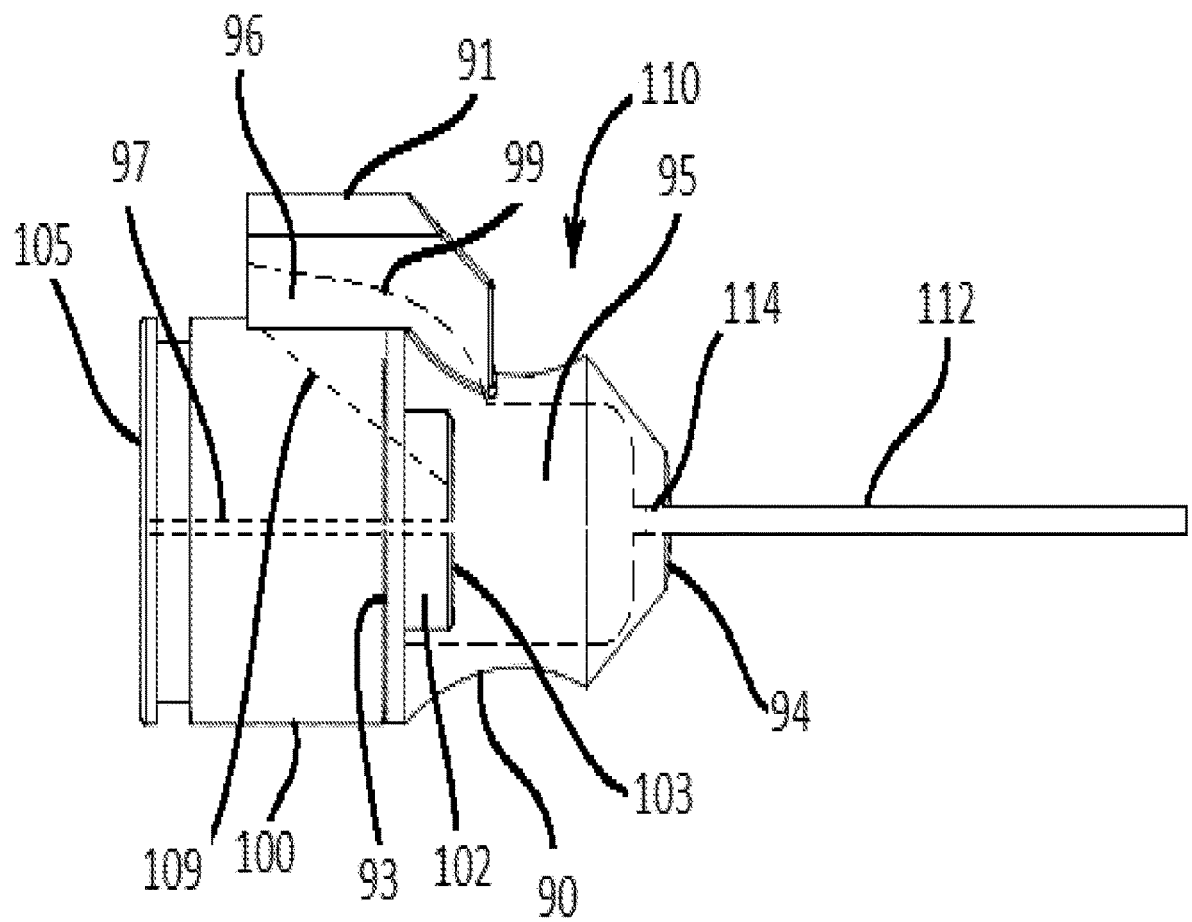
FIG. 11 is a sectional view of an assembled hand piece, including distal and proximal portions, and a probe, of an endoscope according to an exemplary embodiment of the present invention.

Referring to FIGS. 9A, 9B, 9C, 9D and FIGS. 10A, 10B, 10C, 10D, an exemplary embodiment of the present invention provides a hand piece design comprising a distal portion 90 and a proximal portion 100 fixedly assembled to form hand piece, such as hand piece 110 as illustrated for example in FIG. 11. According to an exemplary implementation of embodiments of the present invention distal portion 90 includes an opening 92 terminating at surface 94 of the distal end or portion 90, and an opening 93 terminating at the proximal end of portion 90. Opening 92 is configured for accommodating the proximal end of a probe, such as proximal end 114 of probe 112 as illustrated for example in FIG. 11, which can be fixedly attached to extend distally from surface 94. Opening 93 is configured to interface with the distal end 102 of proximal portion 100 whereby distal portion 90 and proximal portion 100 can be fixedly assembled to form a hand piece, for example as illustrated in FIG. 11. Distal portion 90 contains channel 95 and defines at least a first portion 99 of the inner wall of channel 96 by a protruding section 91, which can also serve as a guide for holding the hand piece. Proximal portion 100 contains channel 97, which extends from surface 103 of distal end 102 and terminates at surface 105 of the proximal end of portion 100. Proximal portion 100 defines at least a second portion 109 of the inner wall of channel 96.

Figure 12:
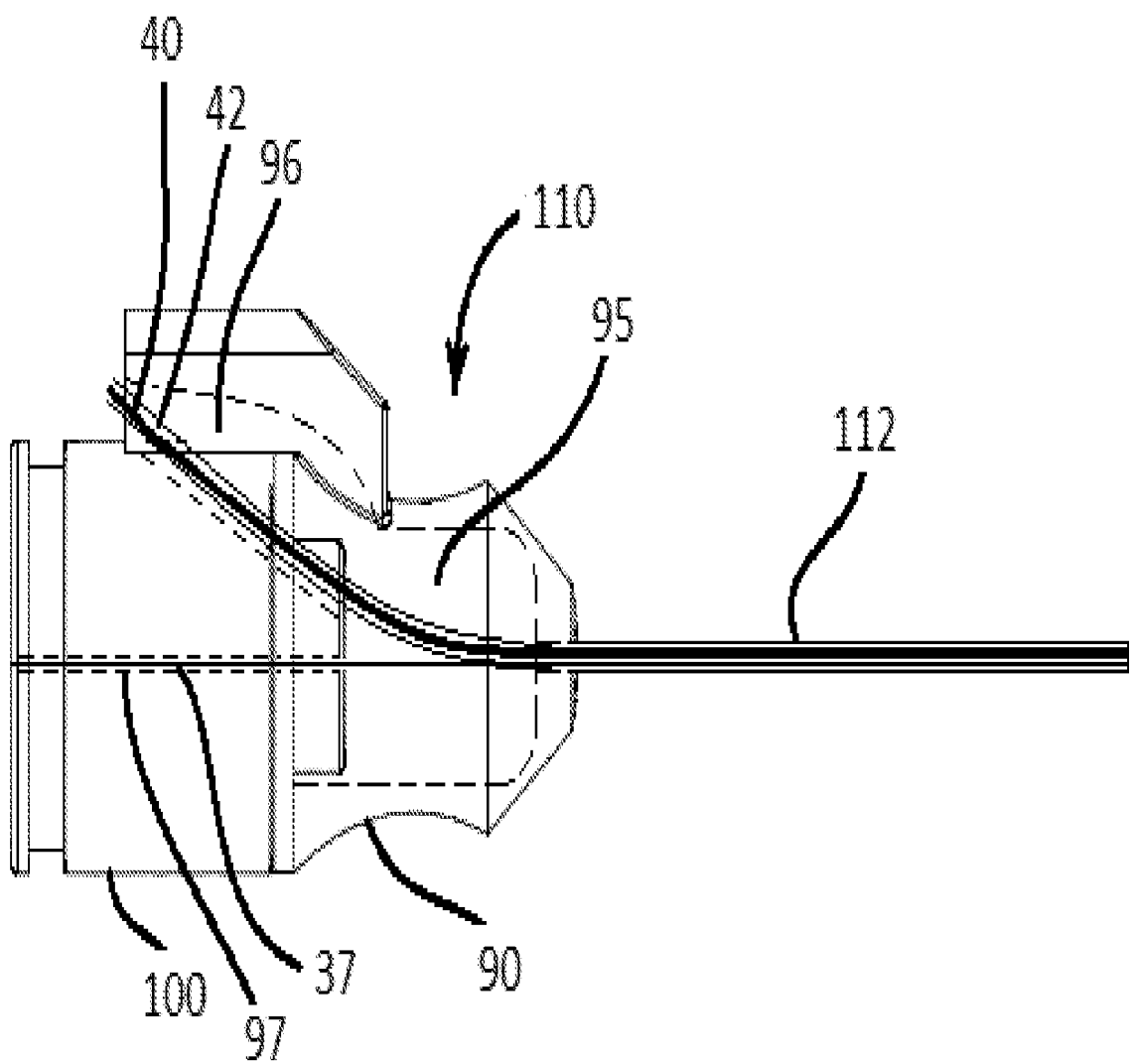
FIG. 12 is a sectional view of an assembled hand piece, including distal and proximal portions, and a probe, showing an exemplary configuration of a laser guide, an illumination guide and an image guide, of an endoscope according to an exemplary embodiment of the present invention.
Figure 13:
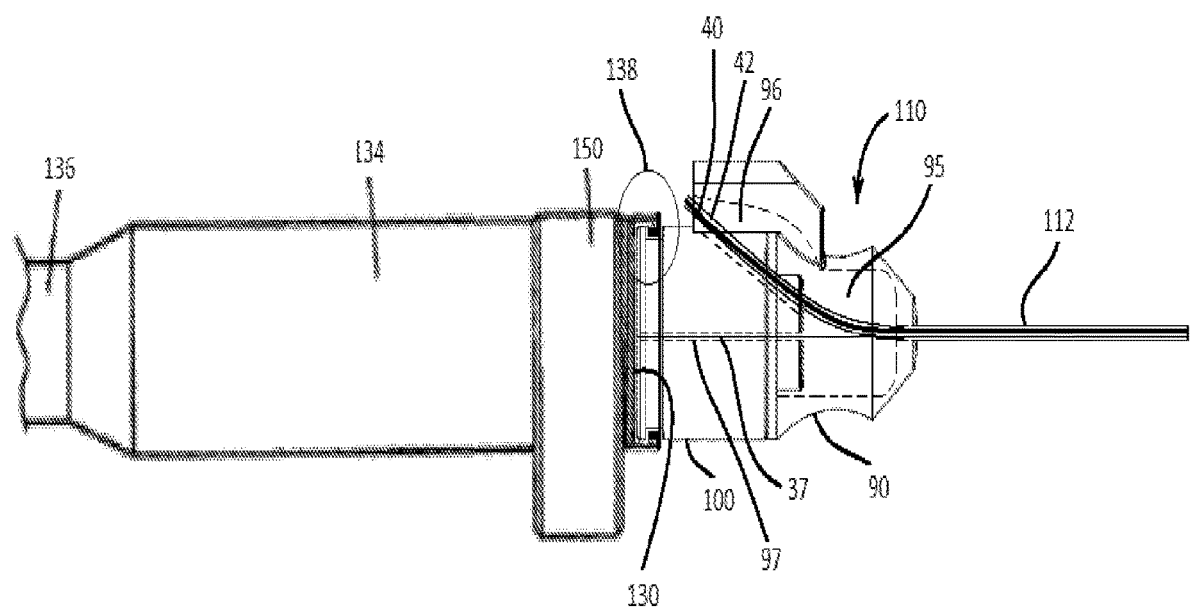
FIG. 13 is a sectional view of an endoscope system including probe, hand piece and camera system, according to an exemplary embodiment of the present invention.

Referring to FIGS. 11, 12, and 13, in an exemplary implementation of embodiments of the present invention, hand piece 120 comprising distal portion 90 and proximal portion 100 separates the image guide fibers 37, laser guide fiber 40, and illumination guide fibers 42 entering channel 95 at the distal end of distal portion 90 from the proximal end 114 of probe 112, such that only image guide fibers 37 extend through channel 97, while the laser guide fiber 40 and the illumination guide fibers 42 extend through channel 96. Channel 97 terminates at surface 105 at the proximal end of proximal portion 100 and is used to optically couple the image guide fibers 97 extending from distal end of probe 112 to the lens or input optics 130 of the camera assembly 134. Channel 96 terminates at exterior side surface 101 of proximal portion 100 and is used to accommodate the laser guide fiber 40 and the illumination guide fibers 42 extending from the distal end of probe 112 to be carried proximately by a cable, such as cable 38.

In an exemplary implementation of embodiments of the present invention, camera assembly 134 can provide an electrical image that is transmitted proximally along the electrical cable 136 connected at the output of camera assembly 134.

In another exemplary implementation of embodiments of the present invention, a connection 138 of camera assembly 134 with hand piece 110 can comprise, for example, a snap fit connection achieved by physical characteristics of the proximal end of proximal portion 100 and the distal end of camera assembly 135 to facilitate readily mounting the camera assembly 134 to the hand piece 110 and readily removing the camera assembly 134 from the hand piece 110.

In yet another exemplary implementation, the camera assembly 134 can include a focus ring 150 to assure adequate focus of the image provided onto the image receptors of the camera assembly 134 positioned at the proximal end of the image guide fibers 37 which extends from the distal end of the probe 30 and through channels 95 and 97 of the hand piece 110.

Figure 14:
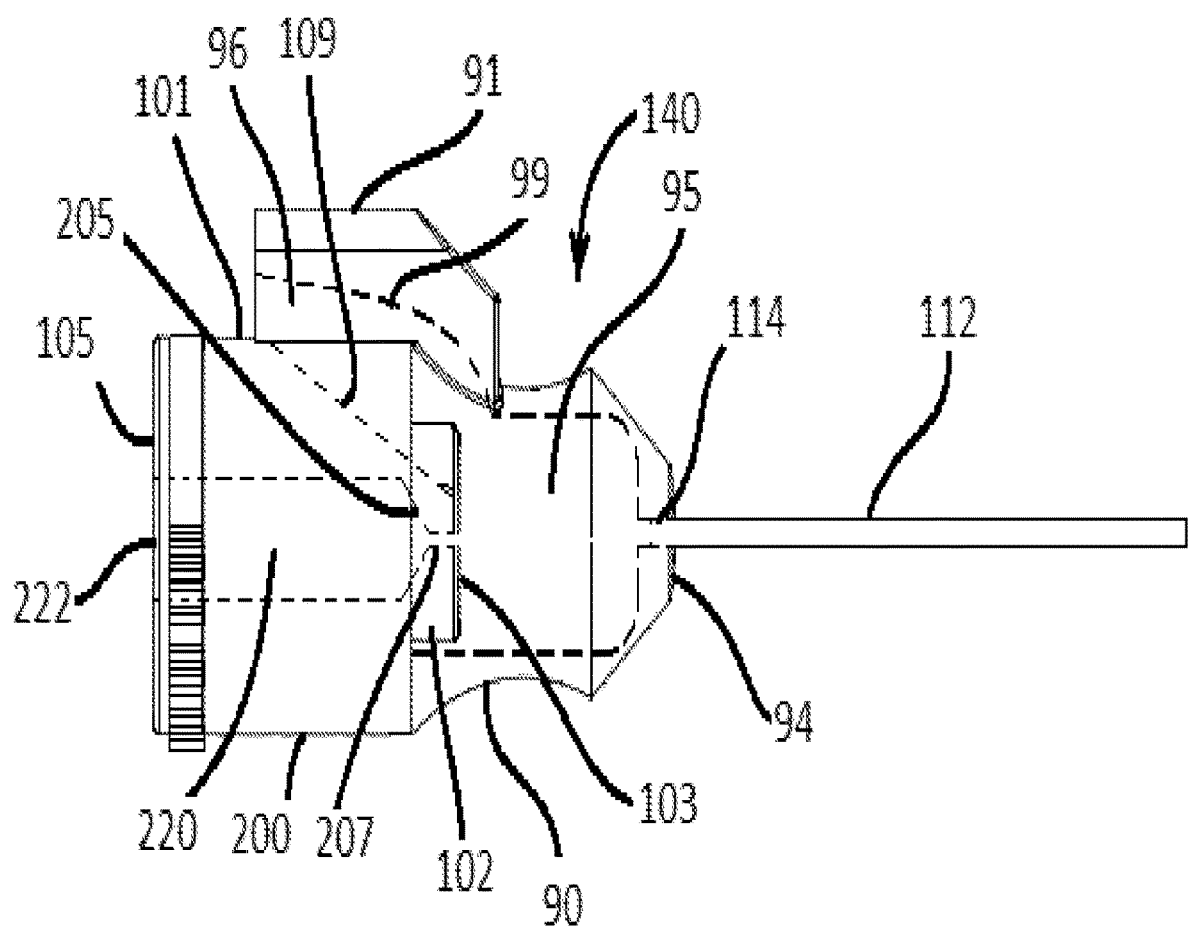
FIG. 14 is a sectional view of an assembled hand piece, including distal and proximal portions, and a probe, of an endoscope according to another exemplary embodiment of the present invention.
Figure 15:
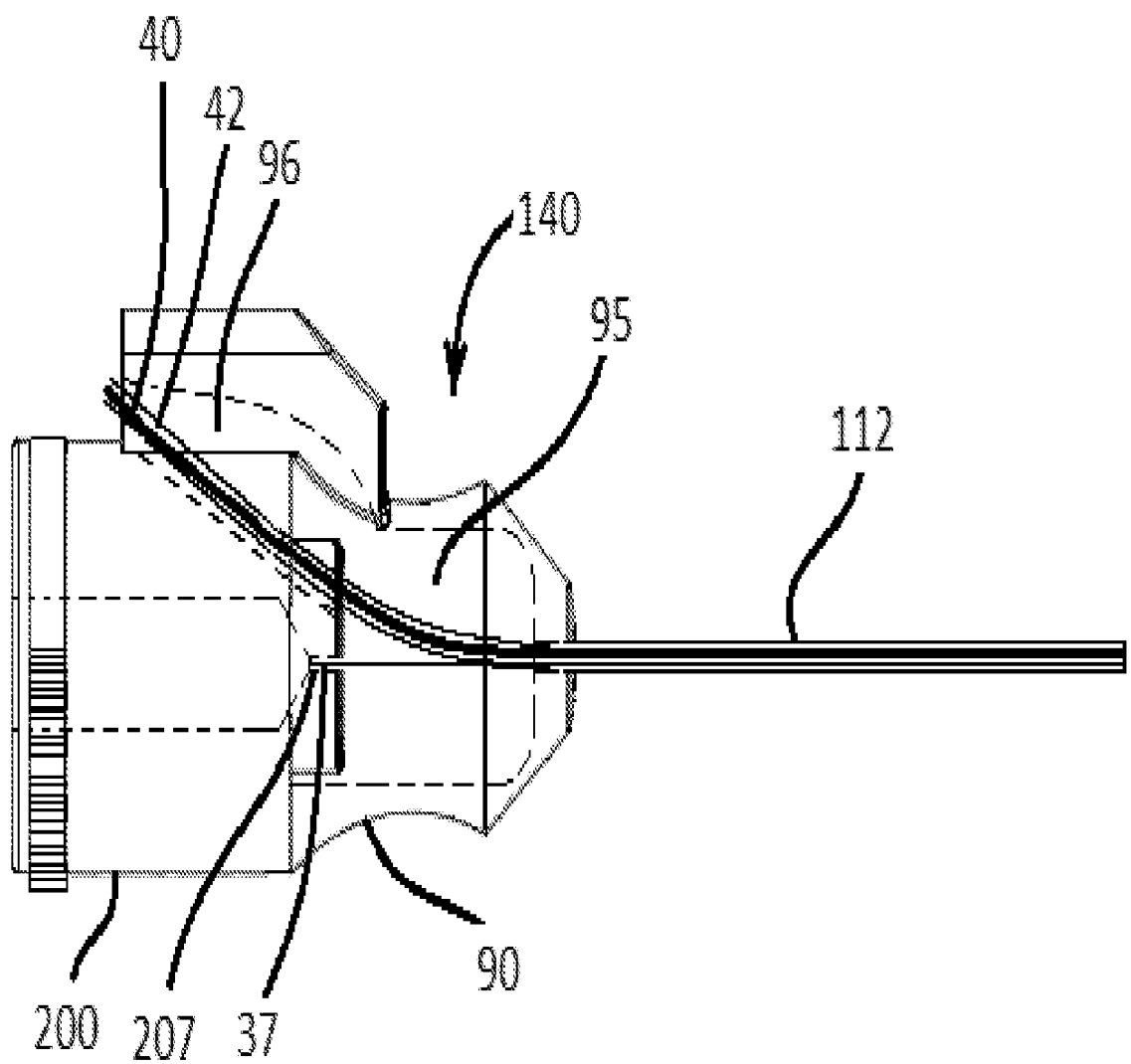
FIG. 15 is a sectional view of an assembled hand piece, including distal and proximal portions, and a probe, showing an exemplary configuration of a laser guide, an illumination guide and an image guide, of an endoscope according to another exemplary embodiment of the present invention.
Figure 16:
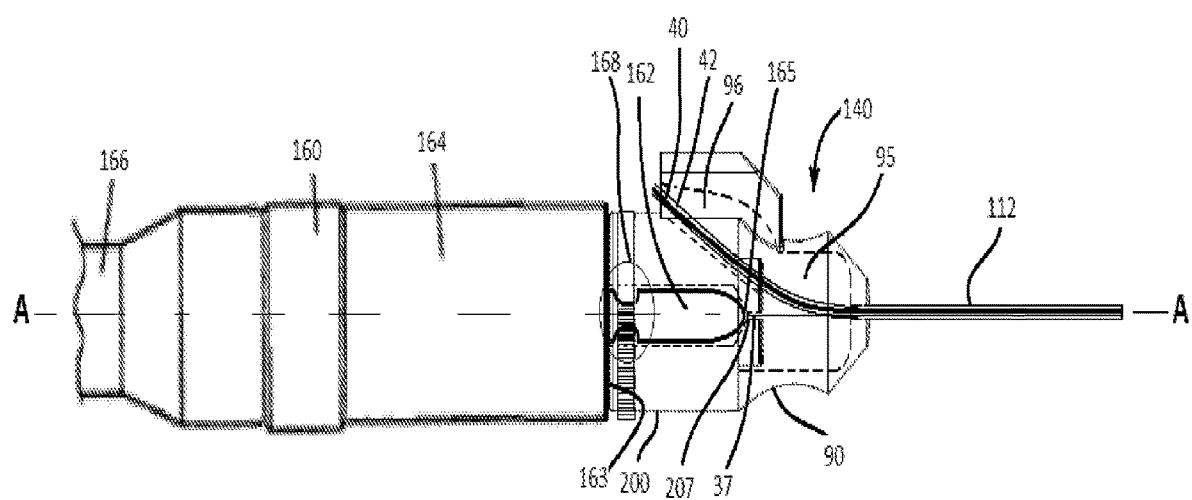
FIG. 16 is a sectional view of an endoscope system including probe, hand piece and camera system, according to another exemplary embodiment of the present invention.

Referring to FIGS. 14, 15, and 16, in an exemplary implementation of embodiments of the present invention, hand piece 140 comprising distal portion 90 and proximal portion 200 separates the image guide fibers 37, laser guide fiber 40, and illumination guide fibers 42 entering channel 95 at the distal end of distal portion 90 from the proximal end 114 of probe 112, such that only image guide fibers 37 extend through channel 207, while the laser guide fiber 40 and the illumination guide fibers 42 extend through channel 96. In contrast to exemplary embodiment of FIGS. 11, 12 and 13, channel 207 terminates at surface 205 at distal end of a cavity 220 having an opening 222 at proximal end face 105 of portion 200. Channel 207 is used to optically couple the image guide fibers 97 extending from distal end of probe 112 to the lens or input optics 165 disposed in a protruding portion 162, which extends distally from surface 163 of the camera assembly 164 into cavity 220 of hand piece 140. Channel 96 terminates at exterior side surface 101 of proximal portion 200 and is used to accommodate the laser guide fiber 40 and the illumination guide fibers 42 extending from the distal end of probe 112 to be carried proximately by a cable, such as cable 38.

In an exemplary implementation of embodiments of the present invention, camera assembly 164 can provide an electrical image that is transmitted proximally along the electrical cable 166 connected at the output of camera assembly 164.

In another exemplary implementation of embodiments of the present invention, a connection 168 of camera assembly 164 with hand piece 140 can comprise, for example, a snap fit connection achieved when protruding portion 162 is inserted into cavity 220 to facilitate readily mounting the camera assembly 164 to the hand piece 140 and readily removing the camera assembly 164 from the hand piece 140. In an exemplary implementation, connection 168 allows hand piece 140 and probe 112 to be axially rotated (about axis A-A) with respect to camera assembly 164.

In yet another exemplary implementation of the embodiments of the present invention, image output from the image guide 37 of a probe 112 can be properly oriented in the camera assembly 164 for display and/or further image processing output via electrical cable 166 connected at the output of camera assembly 164. Such desired orientation of the image for display and/or further image processing can be performed through electronic image processing, or optically, using components disposed within camera assembly 164 or connected to cable 166 at output of camera assembly 164, or any combination thereof. For example, when the hand piece 140 is connected to the camera assembly 164 no manual orientation of probe 112 with respect to subject such as an operating site (not shown) at distal end of probe 112 is needed. Endoscope user can rotate probe 112 with respect to the subject by rotating hand piece 140, which rotates with respect to the camera assembly 164, without disrupting the image of the subject, which may be particularly advantageous when using a curved endoscopes.

In yet another exemplary implementation, the camera assembly 164 can include a focus ring 160 to assure adequate focus of the image provided onto the image receptors of the camera assembly 164 positioned at the proximal end of the image guide fibers 37 which extends from the distal end of the probe 30 and through channels 95 and 97 of the hand piece 110.

Figure 17:
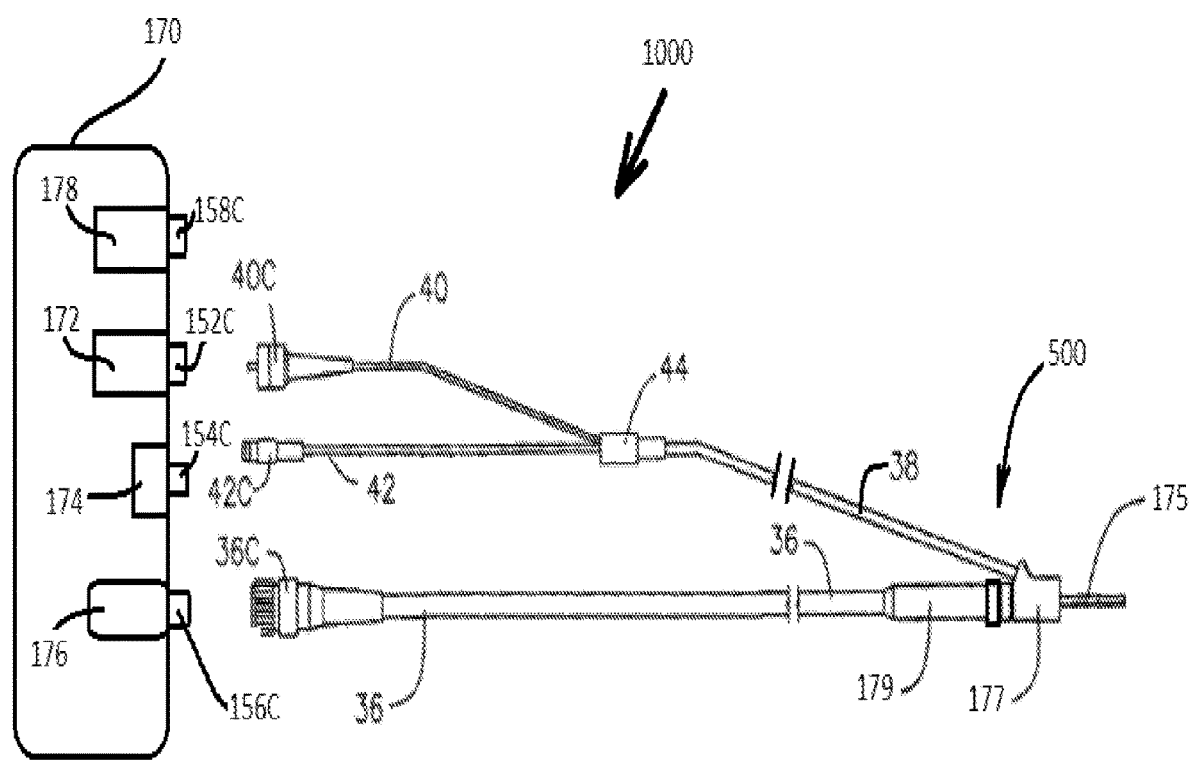
FIG. 17 is a schematic diagram illustrating components of an endoscopy system according to exemplary embodiments of the present invention including illumination source, laser energy source, and image processing and/or display device interface.

Referring to conceptual diagram of FIG. 17, an exemplary embodiment of the present invention provides a system 1000 comprising a console 170 and an endoscope 500 including camera assembly 179, hand piece 177 and probe 175 which can be configured and constructed in various combinations of exemplary implementations of camera assembly, hand piece, and probe as described herein with reference to FIGS. 2 through 16.

In an exemplary implementation of the embodiments of the present invention, console 170 can comprise one or any combination of multiple laser energy sources 172 and/or 178 for connection to laser guide fiber 40 via, for example uniquely configured connectors 152C and/or 158C respectively, one or more illumination light sources 174 for connection to illumination guide fibers 42 via connector 154C, and one or more image display or image processing interfaces 176 for connection to image guide fibers 37 via connector 156C. For example, laser energy source 172 can be a 532 nm laser source which can be connected to endoscope 500 whose probe is configured as in the example of FIGS. 7 and 8, while laser energy source 178 can be a 810 nm laser source which can be connected to endoscope 500 whose probe is configured as in the example of FIG. 2, FIG. 13, or FIG. 16 (notably, any of the hand pieces in FIG. 2, 13 or 16 can be configured with a probe of FIGS. 7 and 8).

Further, referring to example of FIG. 17, image output from image guide fibers 37 of probe 175 can be oriented in the camera assembly 179 using components disposed within camera assembly 179, components disposed within image processing interface 176, and/or other components of console 170, so that when hand piece 177 is connected to camera assembly 179 no manual image orientation is needed and the user can rotate probe 175 with respect to camera assembly 179 without disrupting the image output by manipulating hand piece 177.

While the present invention has been shown and described with reference to certain exemplary embodiments thereof, it will be understood by those skilled in the art that various changes in form and details may be made therein without departing from the spirit and scope of the present invention and the scope of the claims.

What is claimed is:

1. A laser video endoscope for ophthalmologic surgery comprising:
a rigid hand piece having proximal and distal ends, a first open channel extending between the proximal and distal ends, and, a second open channel extending at a non-zero angle from the first open channel and terminating at a hand piece surface, wherein a longitudinal axis of the first open channel intersects with a longitudinal axis of the second open channel at a juncture located along the first open channel, and, wherein said first open channel includes a first reduced-diameter portion extending distally from the proximal end, the first reduced-diameter portion being defined by surrounding solid portions of the hand piece;
a hollow rigid probe extending distally of the distal end of the hand piece, said probe having a distal portion and a proximal portion, said probe containing a laser guide fiber, an imaging component, and an illumination fiber bundle, wherein said laser guide fiber is adapted to transmit laser energy;
a camera assembly rigidly coupled to the proximal end of the hand piece; and,
a blocking filter located to span across the first open channel at the proximal end of the hand piece, configured to block said laser energy,
wherein said laser guide fiber, said imaging component, and said illumination bundle extend proximally from said proximal portion of said probe and into said first open channel with said laser guide fiber and said illumination bundle extending into said second open channel and with said imaging component extending through said juncture and said first reduced-diameter portion to the proximal end, adjacent to the blocking filter, said first reduced-diameter portion being dimensioned to minimize lateral misalignment between said imaging component and the blocking filter, and,
wherein a first length of said imaging component extends from said juncture to adjacent to the blocking filter, a majority of said first length being received within said first reduced-diameter portion.

2. The endoscope of claim 1 wherein:
said laser guide fiber being approximately 100 microns in diameter, and
said imaging component being approximately 14 mils in diameter.

3. The endoscope of claim 1, wherein said proximal portion of said probe having at least an approximately 35 mil outer diameter and at least an approximately five mil thick sidewall.

4. The endoscope of claim 1, wherein said proximal portion of said probe has a length of 120 mils.

5. The endoscope of claim 1, wherein said imaging component comprises a fiber optic bundle having approximately 6,000 fibers.

6. The endoscope of claim 1, wherein said illumination fiber bundle comprises approximately 70 fibers essentially surrounding said laser guide fiber and said imaging component.

7. The endoscope of claim 1, wherein said probe is metal.

8. The endoscope of claim 1, wherein an output of said imaging component is adapted by the camera assembly to be transmitted to a remote display.

* * * * *